(12) United States Patent
Keil et al.

(10) Patent No.: US 9,079,862 B2
(45) Date of Patent: Jul. 14, 2015

(54) PROCESS FOR PREPARING ACETANILIDES

(71) Applicants: Michael Keil, Freinsheim (DE); Wolfgang Reichert, Frankenthal (DE); Christopher Koradin, Ludwigshafen (DE); Yüksel Battal, Ludwigshafen (DE)

(72) Inventors: Michael Keil, Freinsheim (DE); Wolfgang Reichert, Frankenthal (DE); Christopher Koradin, Ludwigshafen (DE); Yüksel Battal, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/371,755

(22) PCT Filed: Dec. 13, 2012

(86) PCT No.: PCT/EP2012/075345
§ 371 (c)(1),
(2) Date: Jul. 11, 2014

(87) PCT Pub. No.: WO2013/104478
PCT Pub. Date: Jul. 18, 2013

(65) Prior Publication Data
US 2014/0364623 A1 Dec. 11, 2014

Related U.S. Application Data

(60) Provisional application No. 61/586,143, filed on Jan. 13, 2012.

(30) Foreign Application Priority Data

Jan. 13, 2012 (EP) .................................... 12151127

(51) Int. Cl.
*C07C 211/48* (2006.01)
*C07D 231/12* (2006.01)

(52) U.S. Cl.
CPC ............ *C07D 231/12* (2013.01); *C07C 211/48* (2013.01)

(58) Field of Classification Search
CPC ............................ C07D 231/12; C07D 211/48
USPC ....................................................... 548/375.1
See application file for complete search history.

(56) References Cited

U.S. PATENT DOCUMENTS

| 3,630,716 A | 12/1971 | Olin |
| 3,637,847 A | 1/1972 | Olin |
| 4,249,935 A | 2/1981 | Eicken et al. |
| 4,321,395 A | 3/1982 | Eicken et al. |
| 4,517,011 A | 5/1985 | Thomas et al. |
| 4,593,104 A | 6/1986 | Eicken et al. |

FOREIGN PATENT DOCUMENTS

| AU | 519478 | 12/1981 |
| CA | 1 120 043 | 3/1982 |
| DE | 26 48 008 | 5/1978 |
| DE | 27 04 281 | 8/1978 |
| DE | 27 44 396 | 4/1979 |
| DE | 28 30 764 | 1/1980 |
| DE | 28 49 442 | 5/1980 |
| EP | 0 001 751 | 5/1979 |
| EP | 0 012 216 | 6/1980 |
| EP | 0 036 544 | 9/1981 |
| IN | 188916 | 11/2002 |

OTHER PUBLICATIONS

International Search Report, PCT/EP2012/075345, filed Dec. 13, 2012, search completed Jan. 21, 2013.
International Preliminary Report on Patentability, PCT/EP2012/075345, filed Dec. 13, 3012, report issued Jul. 15, 2014.

*Primary Examiner* — Samantha Shterengarts
(74) *Attorney, Agent, or Firm* — Brinks Gilson & Lione

(57) ABSTRACT

The present invention relates to a novel process for preparing acetanilides of the formula (I)

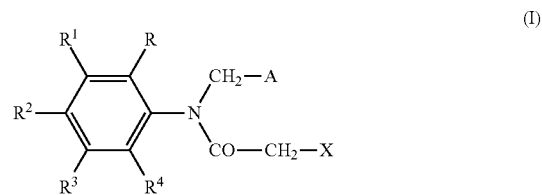

by reacting a 2-halo-N-halomethylacetanilide of the formula (II)

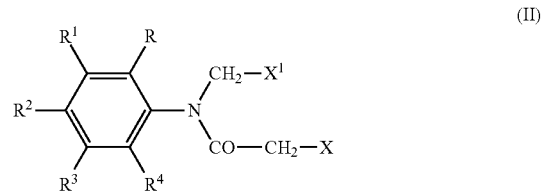

with an azole of the formula (III)

H-A     (III)

wherein the substituents R, $R^1$, $R^2$, $R^3$, $R^4$, A, X and $X^1$ in the formulae (I), (II) and (III) have the meanings as indicated in the description.

15 Claims, No Drawings

PROCESS FOR PREPARING ACETANILIDES

This application is a National Stage application of International Application No. PCT/EP2012/075345, filed Dec. 13, 2012, which claims the benefit of U.S. Provisional Application No. 61/586,143, filed Jan. 13, 2012, the entire contents of which are hereby incorporated herein by reference. This application also claims priority under 35 U.S.C. §119 to EP Patent Application No. 12151127.3, filed Jan. 13, 2012, the entire contents of which is hereby incorporated herein by reference.

The present invention relates to a process for preparing acetanilides of the formula (I)

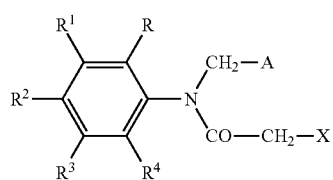

by reacting a 2-halo-N-halomethylacetanilide of the formula (II)

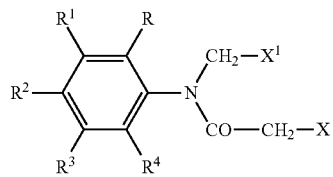

with an azole of the formula (III)

wherein the substituents R, $R^1$, $R^2$, $R^3$, $R^4$, A, X and $X^1$ in the formulae I, II and III have the meanings indicated below.

Acetanilides of the formula I are known as herbicidal active ingredients (see, e.g. DE-OS No. 26 48 008, DE-OS No. 27 04 281, DE-OS 2704281, DE-OS No. 28 30 764, DE-OS No. 28 49 442, U.S. Pat. No. 4,249,935, EP-A-12 216). In particular, 2-chloro-N-(2,6-dimethylphenyl)-N-(1H-pyrazol-1-ylmethyl)-acetamide (common name: Metazachlor) is a widely applied herbicide which is selectively used against weeds in a variety of crops.

German Laid-Open Applications Nos. DE-OS 2648008, DE-OS 2704281 and DE-OS 2744396 already describe the preparation of 2-halo-N-halomethylacetanilides by reacting a 2-halo-N-halomethyl acetanilides with an azole. The hydrogen halide liberated during the reaction needs to be intercepted by acid-binding agents such as organic or inorganic bases. It is also possible to use an excess of the azole as the acid-binding agent. Alternatively, the 2-halo-N-halomethylacetanilide can be reacted with a previously prepared metal salt of the azole.

CA 1,120,043 discloses that substituted N-methyl-pyrazole acetanilides can be purified by treating the crude products resulting from their synthesis with concentrated aqueous solutions of strong acids (such as sulfuric acid or hydrochloric acid), separating off the aqueous solution, diluting with water, and separating the resulting precipitate from the aqueous fluid.

IN 188916 discloses a process for the purification of 2-chloro-N-(2,6-dimethylphenyl)-N-(1H-pyrazol-1-ylmethyl)-acetamide (Metazachlor) containing 2-chloro-N-(2,6-dimethylphenyl)acetamide as an impurity. The process is carried out by treating a solution of crude Metazachlor with methanesulfonic acid so as to precipitate metazachlor methanesulfonate, separating the metazachlor methanesulfonate from the slurry, dissolving the resulting solid in methanol and neutralizing with alcoholic sodium hydroxide to precipitate the sodium salt of methanesulfonic acid and free Metazachlor which remains in solution. The sodium salt of methanesulfonic acid is filtered off and the filtrate containing metazachlor is concentrated and the residual mass is triturated with hexane to give metazachlor in monoclinic crystalline form which is isolated by filtration.

U.S. Pat. No. 4,321,395 discloses the preparation of 2-halo-N-halomethylacetanilides by reacting the 2-halo-N-halomethylacetanilide with the azole in the presence of an at least one molar amount of an aqueous alkali such as sodium hydroxide in a two-phase system, optionally in the presence of a phase transfer catalyst.

All these known methods usually involve tedious work-up, purifications and wastewater treatment steps and difficulties in the isolation of the desired product and the recovery of starting materials (e.g. when recovering excess amounts of the azole), especially on an industrial scale. Moreover, these methods do not always provide the desired acetanilides I (in particular Metazachlor) in a sufficiently high yield and/or purity.

It is therefore an object of the present invention to provide an improved process for preparing the acetanilides I (e.g. Metazachlor) which allows an economical and industrially more feasible preparation of the desired product. It is a further object to provide such a process in which the desired product is obtained in high yield and purity.

These objects are in part or in whole achieved by a process for preparing acetanilides of the formula (I)

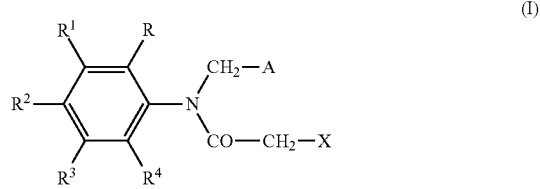

where the substituents are each defined as follows:
R, $R^1$, $R^2$, $R^3$, $R^4$ is each independently selected from the group consisting of hydrogen, halogen, $C_1$-$C_4$-alkyl, and $C_1$-$C_4$-alkoxy;
X is halogen; and
A is an azolyl group which is bonded via a ring nitrogen and may be substituted on its ring members by 1, 2 or 3 substituents independently selected from the group consisting of halogen, cyano, phenyl, $C_1$-$C_4$-alkyl, $C_1$-$C_4$-alkoxy, $C_1$-$C_4$-alkylthio, and $C_1$-$C_4$-carboalkoxy; which comprises:

a) providing a substantially anhydrous reaction mixture comprising a halomethyl compound of the formula (II)

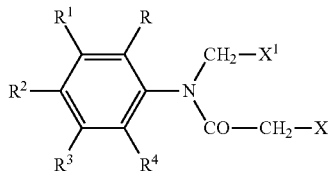

(II)

where R, $R^1$, $R^2$, $R^3$, $R^4$ and X have the same meanings as defined above and $X^1$ is halogen,
an azole of the formula (III)

H-A  (III)

where A has the same meaning as defined above and a substantially anhydrous inert organic solvent, reacting the halomethyl compound (II) with the azole (III) and removing the compound H—$X^1$ formed during the reaction from the reaction mixture by subjecting the reaction mixture to a reduced pressure, heating the reaction mixture, or a combination of the aforementioned measures, and
b) isolating the acetanilide of the formula (I).

It has now surprisingly been found that the process according to the invention provides the desired acetanilides of the formula I (e.g. Metazachlor) in high yield and purity without tedious work-up, purification and wastewater treatment steps and difficulties in the isolation of the desired product and the recovery of starting materials.

One particular advantage is that the process of this invention can be performed under anhydrous conditions without the need of using acid-binding agents such as organic or inorganic bases for scavenging the hydrogen halide (e.g. HCl) liberated during the reaction. Moreover, the process of this invention provides the advantage that it does not require the use of relatively expensive phase transfer catalysts. Furthermore, tedious purification, treatment and/or disposal of wastewater containing non-reacted azole (III), such as e.g. pyrazole, can be avoided. The process of this invention also offers the possibility of isolating the desired acetanilide (I), especially Metazachlor, by direct crystallization from the reaction mixture and recovery of the crystalline end product.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the substituents R, $R^1$, $R^2$, $R^3$ and $R^4$ are—like the term halogen in case of the substituents X and $X^1$—collective terms for individual enumerations of the individual group members. All hydrocarbon chains, i.e. all alkyl, can be straight-chain or branched, the prefix $C_n$-$C_m$ denoting in each case the possible number of carbon atoms in the group.

The term "halogen" in each case denotes fluorine, chlorine, bromine or iodine, preferably chlorine.

The term "$C_1$-$C_4$-alkyl", as used herein, denotes a saturated straight-chain or branched hydrocarbon group comprising from 1 to 4 carbon atoms, for example methyl, ethyl, propyl, 1-methylethyl, butyl, 1-methylpropyl, 2-methylpropyl or 1,1-dimethylethyl, in particular methyl.

"$C_1$-$C_4$-alkoxy" represents, for example, methoxy, ethoxy, n-propoxy, 1-methylethoxy, n-butoxy, 1-methylpropoxy, 2-methylpropoxy or 1,1-dimethylethoxy, especially 1-methylethoxy.

"$C_1$-$C_4$-alkylthio" represents, for example, methylthio, ethylthio, propylthio, 1-methylethylthio, butylthio, 1-methylpropylthio, 2-methylpropylthio and 1,1-dimethylethylthio "$C_1$-$C_4$-carboalkoxy" represents, for example, carbomethoxy and carboethoxy.

The advantages of the process according to the invention become particularly apparent when, in the compounds of formulae (I), (II) and (III), the substituents are each independently defined as follows, more preferably in combination:
R is $C_1$-$C_4$-alkyl, in particular methyl;
$R^1$ is hydrogen;
$R^2$ is hydrogen;
$R^3$ is hydrogen;
$R^4$ is $C_1$-$C_4$-alkyl, in particular methyl;
X is bromine or chlorine, in particular chlorine;
$X^1$ is bromine or chlorine, in particular chlorine;
A is an imidazolyl, pyrrolyl, pyrazolyl, triazolyl, or tetrazolyl group which is bonded via a ring nitrogen and may be substituted on its ring members by 1, 2 or 3 substituents independently selected from the group consisting of halogen, phenyl, methyl, ethyl, isopropyl, methoxy, and cyano.

More preferably, A is a pyrazolyl group which is bonded via a ring nitrogen and may be substituted on its ring members by 1, 2 or 3 substituents independently selected from the group consisting of halogen, phenyl, methyl, ethyl, isopropyl, methoxy, and cyano.

In particular, A is an unsubstituted pyrazolyl group which is bonded via a ring nitrogen.

A particularly preferred embodiment relates to the preparation of an acetanilide of formula (I) wherein
R, $R^4$ are both methyl;
$R^1$, $R^2$, $R^3$ are all hydrogen;
X is chlorine;
$X^1$ is chlorine; and
A is an unsubstituted pyrazolyl group which is bonded via a ring nitrogen.

This compound corresponds to 2-Chloro-N-(2,6-dimethylphenyl)-N-(1H-pyrazol-1-ylmethyl)acetamide of the formula (I-1)

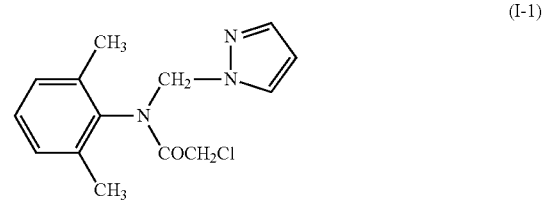

(I-1)

2-Chloro-N-(2,6-dimethylphenyl)-N-(1H-pyrazol-1-ylmethyl)acetamide of the formula (I-1) is also known under the common name Metazachlor, see, for example, The Compendium of Pesticide Common Names (http://www.alanwood.net/pesticides/).

In a particularly preferred embodiment, the substituents R, $R^1$, $R^2$, $R^3$, $R^4$, X and $X^1$ in the halomethyl compound of the formula (II) have the following meanings:
R, $R^4$ are both methyl;
$R^1$, $R^2$, $R^3$ are all hydrogen;
X, $X^1$ are both chlorine.

This compound corresponds to 2-chloro-N-chloromethyl-2',6'-dimethylacetanilide of the formula (II-1)

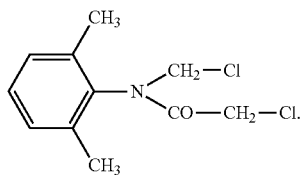

(II-1)

In a particularly preferred embodiment, the azole of the formula (III) is pyrazole of the formula (III-1)

(III-1)

The halomethyl compounds of the formula (II) used as a starting material are known or can be prepared by known methods as illustrated in U.S. Pat. Nos. 3,630,716 and 3,637,847. They are obtained, for example, by reacting the corresponding anilines with paraformaldehyde in the presence of catalytic amounts of potassium hydroxide and adding a halogenoacetyl halide, for example chloroacetyl chloride, to the phenylazomethines formed.

In a preferred embodiment, the halomethyl compound (II) is obtained by reacting an azomethin compound of the formula (IV)

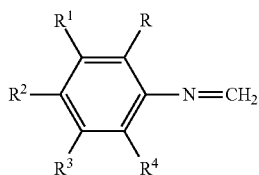

(IV)

where R, R$^1$, R$^2$, R$^3$ and R$^4$ have the same meanings as defined above,
with a haloacetyl halide of the formula (V)

$$X^1\text{—}CO\text{—}CH_2\text{—}X \quad (V)$$

where X and X$^1$ have the same meanings as defined above.

Preferably, the azomethin compound of the formula (IV) is 2,6-dimethyl-N-methylene benzamine of the formula (IV-1)

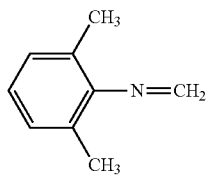

(IV-1)

and the haloacetyl halide of the formula (V) is chloroacetyl chloride of the formula (V-1)

$$Cl\text{—}CO\text{—}CH_2\text{—}Cl \quad (V\text{-}1).$$

Preferably, the azomethin compound (IV), in particular 2,6-dimethyl-N-methylene benzamine (IV-1), is obtained by reacting an aniline compound of the formula (VI)

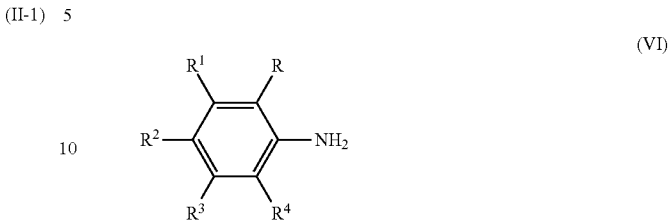

(VI)

where R, R$^1$, R$^2$, R$^3$ and R$^4$ have the same meanings as defined above,
with formaldehyde of the formula (VII)

$$HCOH \quad (VII).$$

In particular, the reaction of the aniline compound (VI) with formaldehyde (VII) is conducted in the substantially anhydrous organic solvent.

In a preferred embodiment, the aniline compound (VI) is 2,6-dimethylaniline of the formula (VI-1)

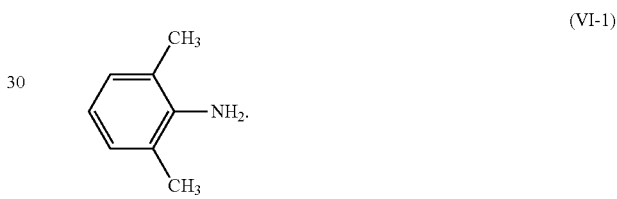

(VI-1)

According to step a) of the process of this invention, a substantially anhydrous reaction mixture comprising a halomethyl compound (II), an azole (III) and a substantially anhydrous inert organic solvent is provided, the halomethyl compound (II) is reacted with the azole (III) and the compound H—X$^1$ formed during the reaction is removed from the reaction mixture by subjecting the reaction mixture to a reduced pressure, heating the reaction mixture, or a combination of the aforementioned measures. In case a combination of the aforementioned measures is selected, they can be performed simultaneously or stepwise in any order.

The substantially anhydrous reaction mixture in step a) may be provided by contacting the halomethyl compound (II), the azole (III) and the substantially anhydrous inert organic solvent in any suitable manner.

Preferably, the halomethyl compound (II) will be initially charged in a reaction vessel, preferably together with the substantially anhydrous inert organic solvent, and the desired reaction conditions will be established. The azole (III) is then added to the halomethyl compound (II). The azole (III) can be added in the form of a solution in the substantially anhydrous inert organic solvent, in solid form, or in the form of a melt. In a preferred embodiment, the azole (III) is added in the form of a solution in the substantially anhydrous inert organic solvent, or in the form of a melt. More preferably, the azole (III) is added in the form of a solution in the substantially anhydrous inert organic solvent in which the halomethyl compound (II) has also been initially charged. It is even more preferred that the azole (III) is added in the form of a melt to the halomethyl compound (II) dissolved in the substantially anhydrous inert organic solvent.

The addition of the azole (III) to the halomethyl compound (II) can be effected at once, portionwise or continuously. The continuous addition of the azole (III) to the halomethyl compound (II) is preferred. In case of first providing a solution of the halomethyl compound (II) in the substantially anhydrous inert organic solvent, the azole (III), in particular in the form of a solution in a substantially anhydrous inert organic solvent, or as a melt, may be added either to the surface of said solution or directly into said solution (as a so-called "immersed" reaction regime).

The reaction time can be varied in a wide range and depends on a variety of factors such as, for example, temperature, pressure, or the equipment used.

For example, the addition of the azole (III), preferably dissolved in the substantially anhydrous inert organic solvent in which halomethyl compound (II) has also been initially charged, is effected typically over the course of from 0.5 to 24 hours, especially from 2 to 10 hours, more preferably from 3 to 8 hours. During this addition time, the reaction of the halomethyl compound (II) with the azole (III) is usually complete. Depending on the selected reaction conditions, a subsequent reaction time of from 0.5 to 18 hours, especially from 1 to 10 hours, more preferably from 1 to 6 hours may still be required to bring the reaction to completion.

The reaction mixture in step a) can also be provided by the previous reaction of the azomethin compound (IV), in particular 2,6-dimethyl-N-methylene benzamine (IV-1), with the haloacetyl halide (V), in particular chloroacetyl chloride (V-1), which has been conducted in the substantially anhydrous inert organic solvent.

Thus, a preferred embodiment of the invention relates to a process for preparing an acetanilide (I), in particular 2-Chloro-N-(2,6-dimethylphenyl)-N-(1H-pyrazol-1-ylmethyl)acetamide (I-1), comprising the steps of $a^\#$) reacting the azomethin compound (IV), in particular 2,6-dimethyl-N-methylene benzamine (IV-1), with the haloacetyl halide (V), in particular chloroacetyl chloride (V-1), in the substantially anhydrous inert organic solvent to provide a substantially anhydrous first mixture comprising the halomethyl compound (II), in particular 2-chloro-N-chloromethyl-2',6'-dimethylacetanilide (II-1);

$a^{\#\#}$) establishing the desired pressure and temperature;

$a^{\#\#\#\#}$) adding the azole (III), in particular pyrazole (III-1), to the first mixture obtained in step a#) to provide a reaction mixture and simultaneously removing the compound H—$X^1$ (in particular hydrogen chloride, HCl) formed during the reaction from the reaction mixture; and b) isolating the acetanilide (I), in particular 2-Chloro-N-(2,6-dimethylphenyl)-N-(1H-pyrazol-1-ylmethyl)acetamide (I-1).

A particularly preferred embodiment of the invention relates to a process for preparing an acetanilide (I), in particular 2-Chloro-N-(2,6-dimethylphenyl)-N-(1H-pyrazol-1-ylmethyl)acetamide (I-1), comprising the steps of $a^{\#1}$) reacting the aniline compound (VI), in particular 2,6-dimethylaniline (VI-1), with formaldehyde (VII) in the substantially anhydrous inert organic solvent to provide a substantially anhydrous first mixture comprising the azomethin compound (IV), in particular 2,6-dimethyl-N-methylene benzamine (IV-1);

$a^{\#2}$) reacting the first mixture obtained in step $a^{\#1}$) with the haloacetyl halide (V), in particular chloroacetyl chloride (V-1), to provide a substantially anhydrous second mixture comprising the halomethyl compound (II), in particular 2-chloro-N-chloromethyl-2',6'-dimethylacetanilide (II-1);

$a^{\#\#\#}$) establishing the desired pressure and temperature;

$a^{\#\#\#\#}$) adding the azole (III), in particular pyrazole (III-1), to the second mixture obtained in step $a^{\#2}$) to provide a reaction mixture and simultaneously removing the compound H—$X^1$ (in particular hydrogen chloride, HCl) formed during the reaction from the reaction mixture; and b) isolating the acetanilide (I), in particular 2-Chloro-N-(2,6-dimethylphenyl)-N-(1H-pyrazol-1-ylmethyl)acetamide (I-1).

Thus, another advantage of the process according to the invention is that the acetanilides (I), in particular Metazachlor, can be obtained in a high yield and purity without isolation of the intermediates of formulae (IV) and/or (II) and purification measures of these intermediates being required.

By "inert organic solvent" is meant an organic solvent which, under the reaction conditions of the process of this invention, does not enter into any appreciable reaction with either the reactants or the products. The term "substantially anhydrous" as used herein means that, although anhydrous inert organic solvents are generally preferred in the reaction mixture, trace amounts of water, such as that often found in commercially available solvents, can be tolerated. Larger amounts of water should be avoided, since the presence of water would lead to an increased consumption of feedstocks.

Preferably, the substantially anhydrous inert organic solvent is an aprotic organic solvent. In particular, the aprotic organic solvent is selected from the group consisting of non-polar aprotic organic solvents, polar aprotic organic solvents, and any mixture thereof. Non-polar aprotic organic solvents are especially preferred. Especially preferable non-polar aprotic solvents include those which have a relative dielectric constant at 20° C. of less than 8, preferably of less than 6 and more preferably of less than 3.

Suitable solvents can be selected from the group consisting of aliphatic hydrocarbons, cycloaliphatic hydrocarbons, aromatic hydrocarbons, halogenated aliphatic hydrocarbons, halogenated aromatic hydrocarbons, amides, ethers, esters, ketones, and any mixture thereof.

Examples of suitable aliphatic hydrocarbons include pentane, hexane, heptane, and the like. Preference is given to saturated aliphatic hydrocarbons having from 5 to 10 carbon atoms.

Examples of suitable cycloaliphatic hydrocarbons include cyclopentane, cyclohexane, cycloheptane, and the like. Preference is given to saturated cycloaliphatic hydrocarbons having from 5 to 10 carbon atoms. Cyclohexane is particularly preferred.

Examples of suitable aromatic hydrocarbons include toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene), and the like. Preference is given to toluene, o-xylene, m-xylene, p-xylene, ethylbenzene, 1,3,5-trimethylbenzene (mesitylene), and any mixture thereof. Especially preferred among the aromatic hydrocarbons are toluene, o-xylene, m-xylene, p-xylene, and any mixture thereof, with toluene being the most preferred.

Examples of suitable halogenated aliphatic hydrocarbons include methylene chloride, chloroform, carbon tetrachloride, 1,2-dichloroethane, 1,1,1,2-tetrachloroethane, 1,1,2,2-tetrachloroethane, 1,1-dichloroethylene, 1,2-dichloroethylene, and the like. Preference is given to 1,1,1,2-tetrachloroethane, 1,1,2,2-tetrachloroethane, 1,1-dichloroethylene, 1,2-dichloroethylene, and any mixture thereof.

Examples of suitable halogenated aromatic hydrocarbons include chlorobenzene, bromobenzene, o-dichlorobenzene, m-dichlorobenzene, and the like. Preference is given to chlorobenzene.

Examples of suitable amides include N,N-dimethylformamide, dimethylacetamide, diethylacetamide, and the like.

Examples of suitable ethers include cyclic and acyclic ethers such as diethyl ether, diisopropyl ether, n-butyl methyl ether, isobutyl methyl ether, sec-butyl methyl ether, tert-butyl methyl ether, tetrahydrofuran, 1,4-dioxane, and the like. Preference is given to tert-butyl methyl ether, tetrahydrofuran, 1,4-dioxane, and any mixture thereof.

Examples of suitable esters include ethyl acetate, n-propylacetate, isopropyl acetate, tert-butyl acetate, and the like.

Examples of suitable ketones include acetone, methyl ethyl ketone, methyl isobutyl ketone, and the like.

In a preferred embodiment, the substantially anhydrous inert organic solvent is selected from the group consisting of aliphatic hydrocarbons, cycloaliphatic hydrocarbons, aromatic hydrocarbons, halogenated aliphatic hydrocarbons, halogenated aromatic hydrocarbons, ethers, and any mixture thereof.

In a more preferred embodiment, the substantially anhydrous inert organic solvent is selected from the group consisting of cycloaliphatic hydrocarbons, aromatic hydrocarbons, halogenated aromatic hydrocarbons, ethers, and any mixture thereof.

Even more preferably, the substantially anhydrous inert organic solvent is selected from the group consisting of cycloaliphatic hydrocarbons, aromatic hydrocarbons, and any mixture thereof.

In another preferred embodiment, the substantially anhydrous inert organic solvent is selected from the group consisting of cyclohexane, toluene, o-xylene, m-xylene, p-xylene, ethylbenzene, 1,3,5-trimethylbenzene (mesitylene), chlorobenzene, 1,1,1,2-tetrachloroethane, 1,1,2,2-tetrachloroethane, 1,1-dichloroethylene, 1,2-dichloroethylene, tert-butyl methyl ether, tetrahydrofuran, 1,4-dioxane, and any mixture thereof.

In an even more preferred embodiment, the substantially anhydrous inert organic solvent is selected from the group consisting of cyclohexane, toluene, o-xylene, m-xylene, p-xylene, chlorobenzene, tetrahydrofuran, 1,4-dioxane, and any mixture thereof.

In an even more preferred embodiment, the substantially anhydrous inert organic solvent is selected from the group consisting of cyclohexane, toluene, and a mixture of cyclohexane and toluene.

Particularly preferred solvents are the aromatic hydrocarbons, especially alkylbenzenes which are mono-, di-, or trialkylsubstituted with each alkyl group containing 1 to 3 carbon atoms, and in particular those selected from the group consisting of toluene, o-xylene, m-xylene, p-xylene, and any mixture thereof. Most preferably, the substantially anhydrous inert organic solvent is toluene.

The process according to this invention has the particular advantage that it does not require the addition of an acid-binding agent as an auxiliary agent. An "acid-binding agent" as used herein is understood to mean any agent which is capable of binding the compound H—$X^1$ (in particular hydrogen chloride, HCl) formed during the reaction of the halomethyl compound (II) with the azole (III), such as, e.g., an auxiliary base like an organic or inorganic base, in particular amines (such as tertiary amines, e.g. pyridine, 2,6-lutidine and triethylamine), alkali metal hydroxides (such as sodium and potassium hydroxide), alkali metal carbonates (such as sodium and potassium carbonate) or alkali metal hydrogencarbonates (such as sodium and potassium hydrogencarbonate). In case the azole (III) itself has acid-binding capacity (such as e.g. pyrazole), it is advantageous that no excess amounts of the azole (III) are required.

Thus, the reaction of the halomethyl compound (II) with the azole (III) is preferably conducted in the absence of an acid-binding agent, in particular in the absence of an auxiliary base.

Moreover, the halomethyl compound (II) is preferably reacted with the azole (III) in essentially equimolar amounts, or the azole (III) is used in a slight excess of up to 10 mol %. The molar ratio of the halomethyl compound (II) to the azole (III) is thus preferably from 1:1 to 1:1.1.

In another embodiment, the compound H—$X^1$ (in particular HCl) formed during the reaction of the halomethyl compound (II) with the azole (III) is removed from the reaction mixture by passing an inert gas through the reaction mixture.

In another embodiment, the compound H—$X^1$ (in particular HCl) formed during the reaction of the halomethyl compound (II) with the azole (III) is removed from the reaction mixture by subjecting the reaction mixture to a reduced pressure and passing an inert gas through the reaction mixture.

In another embodiment, the compound H—$X^1$ (in particular HCl) formed during the reaction of the halomethyl compound (II) with the azole (III) is removed from the reaction mixture by heating the reaction mixture and passing an inert gas through the reaction mixture.

In another embodiment, the compound H—$X^1$ (in particular HCl) formed during the reaction of the halomethyl compound (II) with the azole (III) is removed from the reaction mixture by subjecting the reaction mixture to a reduced pressure, heating the reaction mixture and passing an inert gas through the reaction mixture.

The aforementioned measures can be performed simultaneously or stepwise in any order.

In a preferred embodiment, the compound H—$X^1$ (in particular HCl) is removed from the reaction mixture by subjecting the reaction mixture to a reduced pressure.

In another preferred embodiment, the compound H—$X^1$ (in particular HCl) is removed from the reaction mixture by heating the reaction mixture.

In yet another preferred embodiment, the compound H—$X^1$ (in particular HCl) is removed from the reaction mixture by heating the reaction mixture under a reduced pressure.

In still another preferred embodiment, the pressure and temperature are established such that the reaction mixture is maintained at reflux.

The reaction of the halomethyl compound (II) with the azole (III) can be performed at a pressure in the range of from 0 to 1100 mbar, preferably from 10 to 1000 mbar and in particular from 100 to 500 mbar.

The reaction of the halomethyl compound (II) with the azole (III) can be performed at a temperature in the range of from 20 to 150° C., preferably from 60 to 100° C. and in particular from 70 to 90° C.

In a preferred embodiment, the reaction mixture is maintained at a pressure of from 0 to 900 mbar and a temperature of from 20 to 150° C., preferably at a pressure of from 150 to 600 mbar and a temperature of from 60 to 100° C., especially at a pressure of from 250 to 500 mbar and a temperature of from 70 to 90° C.

The compound H—$X^1$ (in particular HCl) can be removed continuously or stepwise during the course of the reaction. It is also possible to remove the compound H—$X^1$ (in particular HCl) after completion of the reaction. The continuous removal of the compound H—$X^1$ (in particular HCl) during the course of the reaction is preferred.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent;
a2) establishing the desired pressure and temperature; and
a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent selected from aprotic organic solvents, preferably nonpolar aprotic organic solvents and more preferably nonpolar aprotic solvents having a relative dielectric constant at 20° C. of less than 8 (preferably of less than 6 and more preferably of less than 3);
a2) establishing the desired pressure and temperature; and
a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent selected from the group consisting of aliphatic hydrocarbons, cycloaliphatic hydrocarbons, aromatic hydrocarbons, halogenated aliphatic hydrocarbons, halogenated aromatic hydrocarbons, ethers, and any mixture thereof, preferably selected from the group consisting of cycloaliphatic hydrocarbons, aromatic hydrocarbons, halogenated aromatic hydrocarbons, ethers, and any mixture thereof and in particular selected from the group consisting of cycloaliphatic hydrocarbons, aromatic hydrocarbons, and any mixture thereof;
a2) establishing the desired pressure and temperature; and
a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent selected from the group consisting of cyclohexane, toluene, o-xylene, m-xylene, p-xylene, ethylbenzene, 1,3,5-trimethylbenzene (mesitylene), chlorobenzene, 1,1,1,2-tetrachloroethane, 1,1,2,2-tetrachloroethane, 1,1-dichloroethylene, 1,2-dichloroethylene, tert-butyl methyl ether, tetrahydrofuran, 1,4-dioxane, and any mixture thereof, more preferably selected from the group consisting of cyclohexane, toluene, o-xylene, m-xylene, p-xylene, chlorobenzene, tetrahydrofuran, 1,4-dioxane, and any mixture thereof and in particular selected from the group consisting of cyclohexane, toluene, and a mixture of cyclohexane and toluene;
a2) establishing the desired pressure and temperature; and
a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent;
a2) establishing a pressure of from 0 to 900 mbar and a temperature of from 20 to 150° C., preferably a pressure of from 150 to 600 mbar and a temperature of from 60 to 100° C. and especially a pressure of from 250 to 500 mbar and a temperature of from 70 to 90° C.; and
a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent selected from aprotic organic solvents, preferably nonpolar aprotic organic solvents and more preferably nonpolar aprotic solvents having a relative dielectric constant at 20° C. of less than 8 (preferably of less than 6 and more preferably of less than 3);
a2) establishing a pressure of from 0 to 900 mbar and a temperature of from 20 to 150° C., preferably a pressure of from 150 to 600 mbar and a temperature of from 60 to 100° C. and especially a pressure of from 250 to 500 mbar and a temperature of from 70 to 90° C.; and
a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of
a1) providing a substantially anhydrous first mixture comprising the halomethyl compound (II), in particular 2-chloro-N-chloromethyl-2',6'-dimethylacetanilide (II-1), and a substantially anhydrous inert organic solvent selected from the group consisting of aliphatic hydrocarbons, cycloaliphatic hydrocarbons, aromatic hydrocarbons, halogenated aliphatic hydrocarbons, halogenated aromatic hydrocarbons, ethers, and any mixture thereof, preferably selected from the group consisting of cycloaliphatic hydrocarbons, aromatic hydrocarbons, halogenated aromatic hydrocarbons, ethers, and any mixture thereof and in particular selected from the group consisting of cycloaliphatic hydrocarbons, aromatic hydrocarbons, and any mixture thereof;
a2) establishing a pressure of from 0 to 900 mbar and a temperature of from 20 to 150° C., preferably a pressure of from 150 to 600 mbar and a temperature of from 60 to 100° C. and especially a pressure of from 250 to 500 mbar and a temperature of from 70 to 90° C.; and a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In another preferred embodiment, the step a) of the process of this invention is carried out by following the steps of a1) providing a substantially anhydrous first mixture comprising the halomethyl compound (II), in particular 2-chloro-N-chloromethyl-2',6'-dimethylacetanilide (II-1), and a substantially anhydrous inert organic solvent selected from the group consisting of cyclohexane, toluene, o-xylene, m-xylene, p-xylene, ethylbenzene, 1,3,5-trimethylbenzene (mesitylene), chlorobenzene, 1,1,1,2-tetrachloroethane, 1,1,2,2-tetrachloroethane, 1,1-dichloroethylene, 1,2-dichloroethylene, tert-butyl methyl ether, tetrahydrofuran, 1,4-dioxane, and any mixture thereof, more preferably selected from the group consisting of cyclohexane, toluene, o-xylene, m-xylene, p-xylene, chlorobenzene, tetrahydrofuran, 1,4-dioxane, and any mixture thereof and in particular selected from the group consisting of cyclohexane, toluene, and a mixture of cyclohexane and toluene;

a2) establishing a pressure of from 0 to 900 mbar and a temperature of from 20 to 150° C., preferably a pressure of from 150 to 600 mbar and a temperature of from 60 to 100° C. and especially a pressure of from 250 to 500 mbar and a temperature of from 70 to 90° C.; and a3) adding the azole (III), in particular the pyrazole (III-1), to said first mixture to provide the reaction mixture and simultaneously removing the compound H—$X^1$ (in particular hydrogen chloride, HCl) formed during the reaction from the reaction mixture.

In step b) of the process according to this invention, the acetanilide of formula (I), in particular Metazachlor, is preferably isolated in solid form from the reaction mixture obtained in step a) by employing conventional methods, for example by removal of solvent, cooling, concentrating the reaction mixture, adding a co-solvent, adding seed crystals, extraction with a basic or neutral aqueous medium and subsequent crystallization from the organic phase, and the like. The solid acetanilide of formula (I), in particular solid Metazachlor, may be recovered by customary techniques for separating solid components from liquids, for example by filtration, centrifugation or decanting. The solid acetanilide of formula (I) thus isolated may still have higher than desired levels of impurities. The solid may be washed with a suitable solvent or a mixture of solvents, such as, for example, those used in step (a) of the process of this invention, to remove the impurities.

In a preferred embodiment, the acetanilide (I), in particular Metazachlor, is isolated by crystallization from the reaction mixture obtained in step a) to obtain crystals of the acetanilide (I), in particular crystals of Metazachlor, and recovering said crystals to obtain the crystalline acetanilide (I), in particular crystalline Metazachlor. The crystallization of the acetanilide (I), in particular Metazachlor, is preferably effected by concentrating the reaction mixture, adding seed crystals, cooling, or by any combination of the aforementioned measures. In particular, the crystallization of the acetanilides (I), preferably Metazachlor, is effected by distilling off the substantially anhydrous inert organic solvent from the reaction mixture obtained in step a) to provide a concentrated reaction mixture, optionally adding seed crystals to the concentrated reaction mixture, and cooling the concentrated reaction mixture to a temperature lower than 20° C., preferably to a temperature of from −10° C. to 10° C.

In another preferred embodiment, the acetanilide (I), in particular Metazachlor, is isolated by extracting the reaction mixture obtained in step a) with a basic or neutral aqueous medium, subsequent crystallization from the organic phase to obtain crystals of the acetanilide (I), in particular crystals of Metazachlor, and recovering said crystals to obtain the crystalline acetanilide (I), in particular crystalline Metazachlor. In case a basic aqueous medium is used for the extraction, suitable bases for this purpose are alkali metal hydroxides such as sodium and potassium hydroxide, alkali metal carbonates such as sodium and potassium carbonate, alkali metal hydrogencarbonates such as sodium and potassium hydrogencarbonate, alkali metal phosphates such as sodium and potassium phosphate, alkali metal hydrogenphosphates such as sodium and potassium hydrogen-phosphate, alkali metal dihydrogenphosphates such as sodium and potassium dihydrogenphosphate, and also nitrogen bases such as ammonia.

Particular preference is given to the alkali metal hydroxides such as sodium and potassium hydroxide, alkali metal carbonates such as sodium and potassium carbonate, and also to the alkali metal hydrogencarbonates such as sodium and potassium hydrogencarbonate.

The crystalline acetanilide of formula (I), in particular crystalline Metazachlor, is preferably recovered by filtration.

The examples below serve merely to illustrate the invention and are not to be interpreted in a restrictive manner.

The purities reported were determined by means of gas chromatography (GC) or high performance liquid chromatography (HPLC) via the area ratios of the particular peaks.

EXAMPLE 1

Preparation of 2-Chloro-N-(2,6-dimethylphenyl)-N-(1H-pyrazol-1-ylmethyl)acetamide of the formula (I-1) (Metazachlor) by heating the reaction mixture under reduced pressure and using a toluenic solution of pyrazole A solution of 2-chloro-N-chloromethyl-2',6'-dimethylacetanilide, prepared in situ from 2,6-dimethyl-N-methylene benzamine (277.8 g, approx. 1:7.5 w/w in cyclohexane/toluene) that was obtained from formaldehyde and 2,6-dimethylaniline (64.6 g, 575.7 mmol), and chloroacetyl chloride (66.6 g, 590.0 mmol, 1.03 eq) in toluene (50 g), was evacuated to 490 mbar and heated to 90° C. A solution of pyrazole in toluene (10%, 419.2 g, 614.2 mmol, 1.07 eq) was then metered in over a period of 3 hours, and the reaction mixture was then stirred for another 16 hours. The vacuum was broken with nitrogen gas and the reactor cooled down to 25° C. The reaction mixture (741 g) was drained off and a sample was analyzed by quantitative HPLC (19.2 wt %) to yield 89% Metazachlor based on 2,6-dimethylaniline. The reaction mixture was then concentrated by distilling off the solvent (60° C., 100 mbar). The crystallization of Metazachlor was initiated by adding seed crystals to the concentrated reaction mixture which was then cooled to 0° C. Precipitated Metazachlor was filtered off, washed with cyclohexane and dried (116.3 g, >99% purity). The combined mother liquor and wash liquor were again concentrated and crystallized to yield further Metazachlor (18.5 g, 80% purity). The total yield across both crystallizations was 82%.

EXAMPLE 2

Preparation of 2-Chloro-N-(2,6-dimethylphenyl)-N-(1H-pyrazol-1-ylmethyl)acetamide of the formula (I-1) (Metazachlor) by heating the reaction mixture under reduced pressure and using a melt of pyrazole A solution of 2-chloro-N-chloromethyl-2',6'-dimethylacetanilide, prepared in situ from 2,6-dimethyl-N-methylene benzamine (469 g, approx. 1:7.5 w/w in cyclohexane/toluene) that was obtained from formaldehyde and 2,6-dimethylaniline (120.9 g, 997.9 mmol), and chloroacetyl chloride (112.8 g, 998.7 mmol, 1.00 eq) in toluene (85 g) was evacuated to 290 mbar and heated to 74° C. A melt of pyrazole (71.7 g, 1053.1 mmol, 1.05 eq) was then metered in over a period of 6 hours, and the reaction mixture was then stirred for another 6 hours. The reaction mixture was then concentrated by distilling off the solvent (60° C., 100 mbar) to yield a solution of 264.4 g (62.0 wt %, 95% yield based on 2,6-dimethylaniline) Metazachlor. The crystallization of Metazachlor was initiated by adding seed crystals to the concentrated reaction mixture which was then cooled to 0° C. Precipitated Metazachlor was filtered off, washed with cyclohexane and dried (215.0 g, >96% purity). The combined mother liquor and wash liquor were again concentrated and crystallized to yield further Metazachlor (41.0 g, >96% purity). The total yield across both crystallizations was 89%.

EXAMPLE 3

Preparation of 2-Chloro-N-(2,6-dimethylphenyl)-N-(1H-pyrazol-1-ylmethyl)acetamide of the formula (I-1) (Metazachlor) by heating the reaction mixture under normal pressure and using a melt of pyrazole A solution of 2-chloro-N-chloromethyl-2',6'-dimethylacetanilide, prepared in situ from 2,6-dimethyl-N-methylene benzamine (480 g, approx. 1:7.5 w/w in cyclohexane/toluene) that was obtained from formaldehyde and 2,6-dimethylaniline (121.2 g, 1000 mmol), and chloroacetyl chloride (114.1 g, 1010 mmol, 1.01 eq) in toluene (86.5 g) was heated to 114° C. A melt of pyrazole (70.9 g, 1053 mmol, 1.05 eq) was then metered in over a period of 2 hours, and the reaction mixture was then stirred for another 4 hours. The vacuum was broken with nitrogen gas and the reactor cooled down to 25° C. The reaction mixture (690 g) was drained off and a sample was analyzed by quantitative HPLC (35.5 wt %) to yield 88% Metazachlor based on 2,6-dimethylaniline. The reaction mixture was then concentrated by distilling off the solvent (93° C., 280 mbar). The crystallization of Metazachlor was initiated by adding seed crystals to the concentrated reaction mixture which was then cooled to 0° C. Precipitated Metazachlor was filtered off, washed with cyclohexane and dried (189.0 g, >94% purity, yield: 64%).

EXAMPLE 4

Preparation of 2-Chloro-N-(2,6-dimethylphenyl)-N-(1H-pyrazol-1-ylmethyl)acetamide of the formula (I-1) (Metazachlor) by heating the reaction mixture under reduced pressure and using solid pyrazole 470 g of a solution of 2,6-dimethyl-N-methylene benzamine in cyclohexane/toluene (approx. 1:7.5 w/w), prepared in situ from formaldehyde and 2,6-dimethylaniline (121.19 g, 1.0 mol) was converted to 2-chloro-N-chloromethyl-2',6'-dimethylacetanilide by exothermic addition to chloroacetyl chloride (112.9 g, 1.0 mol, 1.00 eq) in toluene (85 g). After cooling to 35° C. crystalline pyrazole (72.3 g, 98 wt-%, 1.04 mol, 1.04 eq) was added to the stirred reaction mixture. After evacuation to 310 mbar the reaction mixture was heated to reflux (75-76° C.; jacket temperature 105° C.). After 4 h the vacuum was adjusted to 450 mbar resulting in a reflux temperature of 86-87° C. After a further period of 4 h the vacuum was broken with nitrogen gas and the reactor was cooled down to 25° C. The reaction mixture was drained off and diluted with toluene used before to flush the reactor. A sample of the diluted reaction mixture (844 g) was analyzed by quantitative GC assay: 29.65 wt-% Metazachlor, i.e. 90.1% yield based on 2,6-dimethylaniline.

EXAMPLE 5

Preparation of 2-Chloro-N-(2,6-dimethylphenyl)-N-(1H-pyrazol-1-ylmethyl)acetamide of the formula (I-1) (Metazachlor) by heating the reaction mixture under reduced pressure and using solid pyrazole 470 g of a solution of 2,6-dimethyl-N-methylene benzamine in cyclohexane/toluene (approx. 1:7.5 w/w), prepared in situ from formaldehyde and 2,6-dimethylaniline (121.19 g, 1.0 mol) was converted to 2-chloro-N-chloromethyl-2',6'-dimethylacetanilide by exothermic addition to chloroacetyl chloride (116.5 g, 1.03 mol, 1.03 eq) in toluene (85 g). In order to remove any unreacted chloroacetyl chloride the reaction mixture was concentrated to about 40% of the original volume at 50° C./40 mbar. The amount of distillate was compensated with fresh toluene and the procedure was repeated once more. After compensating the distillate with fresh toluene crystalline pyrazole (72.3 g, 98 wt-%, 1.04 mol, 1.04 eq) was added to the stirred reaction mixture at 35° C. After evacuation to 290 mbar the reaction mixture was heated to reflux (75-76° C.; jacket temperature 105° C.). After 6 h the vacuum was adjusted to 450 mbar resulting in a reflux temperature of 85-86° C. After a further period of 2 h the vacuum was broken with nitrogen gas and the reactor was cooled down to 25°. The reaction mixture was drained off and diluted with toluene used before to flush the reactor. A sample of the diluted the reaction mixture (926.5 g) was analyzed by quantitative GC assay: 27.22 wt-% Metazachlor, i.e. 90.8% yield based on 2,6-dimethylaniline.

The invention claimed is:

1. A process for preparing acetanilide of the formula (I)

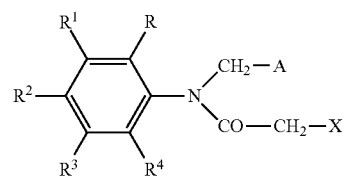

(I)

where the substituents are each defined as follows:

R, $R^1$, $R^2$, $R^3$, $R^4$ is each independently selected from the group consisting of hydrogen, halogen, $C_1$-$C_4$-alkyl, and $C_1$-$C_4$-alkoxy;

X is halogen; and

A is an azolyl group which is bonded via a ring nitrogen and may be substituted on its ring members by 1, 2 or 3 substituents independently selected from the group consisting of halogen, cyano, phenyl, $C_1$-$C_4$-alkyl, $C_1$-$C_4$-alkoxy, $C_1$-$C_4$-alkylthio, and $C_1$-$C_4$-carboalkoxy;

which comprises:

a) providing a substantially anhydrous reaction mixture comprising a halomethyl compound of the formula (II)

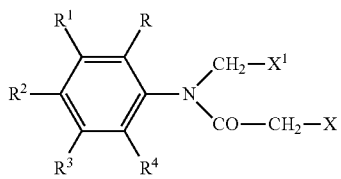

where R, $R^1$, $R^2$, $R^3$, $R^4$ and X have the same meanings as defined above and $X^1$ is halogen,
an azole of the formula (III)

H—A             (III)

where A has the same meaning as defined above and a substantially anhydrous inert organic solvent,
reacting the halomethyl compound (II) with the azole (III) and
removing the compound H—$X^1$ formed during the reaction from the reaction mixture by subjecting the reaction mixture to a reduced pressure, heating the reaction mixture, or a combination of the aforementioned measures, and
b) isolating the acetanilide of the formula (I).

2. The process according to claim 1, wherein
R is $C_1$-$C_4$-alkyl;
$R^1$ is hydrogen;
$R^2$ is hydrogen;
$R^3$ is hydrogen;
$R^4$ is $C_1$-$C_4$-alkyl;
X, $X^1$ are chlorine; and
A is a pyrazolyl group which is bonded via a ring nitrogen and may be substituted on its ring members by 1, 2 or 3 substituents independently selected from the group consisting of halogen, phenyl, methyl, ethyl, isopropyl, methoxy, and cyano.

3. The process according to claim 1, wherein the halomethyl compound (II) is reacted with the azole (III) in substantially equimolar amounts.

4. The process according to claim 3, wherein the molar ratio of the halomethyl compound (II) to the azole (III) is from 1:1 to 1:1.1.

5. The process according to claim 1, wherein the substantially anhydrous inert organic solvent is selected from the group consisting of non-polar aprotic organic solvents, polar aprotic organic solvents, and any mixture thereof.

6. The process according to claim 1, wherein the substantially anhydrous inert organic solvent is selected from the group consisting of aliphatic hydrocarbons, cycloaliphatic hydrocarbons, aromatic hydrocarbons, halogenated aliphatic hydrocarbons, halogenated aromatic hydrocarbons, amides, ethers, esters, ketones, and any mixture thereof.

7. The process according to claim 1, wherein the reaction mixture is maintained at a pressure of from 0 to 900 mbar.

8. The process according to claim 1, wherein the reaction mixture is maintained at a temperature of from 20 to 150° C.

9. The process according to claim 1, wherein a temperature and pressure are established such that the reaction mixture is maintained at reflux.

10. The process according to claim 1, wherein the step a) is carried out by following the steps of
a1) providing a substantially anhydrous first mixture comprising the halomethyl compound (II) and the substantially anhydrous inert organic solvent;
a2) establishing the desired pressure and temperature; and
a3) adding the azole (III) to said first mixture to provide the reaction mixture.

11. The process according to claim 1, wherein the acetanilide of the formula (I) is 2-Chloro-N-(2,6-dimethylphenyl)-N-(1H-pyrazol-1-ylmethyl)acetamide of the formula (I-1)

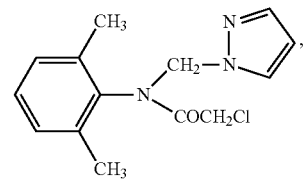

the halomethyl compound of the formula (II) is 2-chloro-N-chloromethyl-2',6'-dimethylacetanilide of the formula (II-1)

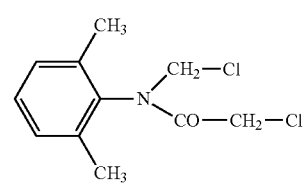

and the azole of the formula (III) is pyrazole of the formula (III-1)

12. The process according to claim 1, wherein the halomethyl compound (II) is obtained by reacting an azomethin compound of the formula (IV)

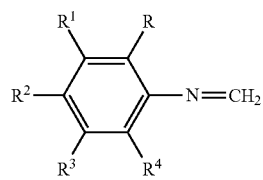

where R, $R^1$, $R^2$, $R^3$ and $R^4$ have the same meanings as defined above,
with a haloacetyl halide of the formula (V)

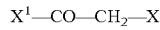

$X^1$—CO—$CH_2$—X             (V)

where X and $X^1$ have the same meanings as defined above.

13. The process according to claim 12, wherein the azomethin compound of the formula (IV) is 2,6-dimethyl-N-methylene benzamine of the formula (IV-1)

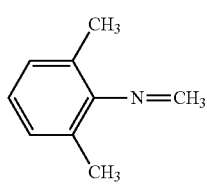
(IV-1)

and the haloacetyl halide of the formula (V) is chloroacetyl chloride of the formula (V-1)

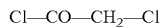
(V-1).

14. The process according to claim 12, wherein the azomethin compound of the formula (IV) is obtained by reacting an aniline compound of the formula (VI)

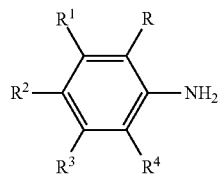
(VI)

where R, $R^1$, $R^2$, $R^3$ and $R^4$ have the same meanings as defined above, with formaldehyde of the formula (VII)

(VII).

15. The process according to claim 14, wherein the aniline compound of the formula (VI) is 2,6-dimethylaniline of the formula (VI-1)

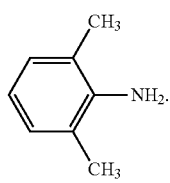
(VI-1)

* * * * *